United States Patent
Stapley et al.

(10) Patent No.: US 10,882,812 B2
(45) Date of Patent: *Jan. 5, 2021

(54) METHOD FOR THE PRODUCTION OF 2,4-DIHYDROXYBUTYRIC ACID

(71) Applicant: DFI USA, LLC, Chaska, MN (US)

(72) Inventors: Jonathan Stapley, Mercer Island, WA (US); David Genders, Lancaster, NY (US)

(73) Assignee: DFI USA, LLC, Mercer Island, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/453,151

(22) Filed: Jun. 26, 2019

(65) Prior Publication Data

US 2020/0002260 A1    Jan. 2, 2020

Related U.S. Application Data

(63) Continuation of application No. 15/738,249, filed as application No. PCT/US2016/039282 on Jun. 24, 2016, now Pat. No. 10,377,691.

(60) Provisional application No. 62/204,796, filed on Aug. 13, 2015, provisional application No. 62/184,571, filed on Jun. 25, 2015.

(51) Int. Cl.

| | |
|---|---|
| C07C 51/235 | (2006.01) |
| C07C 31/18 | (2006.01) |
| C07C 51/00 | (2006.01) |
| C07C 51/16 | (2006.01) |
| C07C 51/377 | (2006.01) |
| C07C 51/295 | (2006.01) |
| C07B 41/08 | (2006.01) |
| C07C 59/10 | (2006.01) |
| C07C 65/03 | (2006.01) |

(52) U.S. Cl.
CPC ............ C07C 51/235 (2013.01); C07B 41/08 (2013.01); C07C 31/18 (2013.01); C07C 51/00 (2013.01); C07C 51/16 (2013.01); C07C 51/295 (2013.01); C07C 51/377 (2013.01); C07C 59/10 (2013.01); C07C 65/03 (2013.01)

(58) Field of Classification Search
CPC ....... C07C 51/295; C07C 59/10; C07C 31/18; C07C 51/00; C07C 51/16; C07C 51/235; C07C 51/377; C07C 65/03; C07B 41/08
See application file for complete search history.

(56) References Cited

U.S. PATENT DOCUMENTS

| | | |
|---|---|---|
| 2007/0181437 A1 | 8/2007 | Stapley et al. |
| 2015/0159182 A1 | 6/2015 | Walther et al. |

FOREIGN PATENT DOCUMENTS

| | | | |
|---|---|---|---|
| EP | 0381527 A1 | | 8/1990 |
| WO | WO2015/033159 | * | 3/2015 |
| WO | WO 2015/033159 | | 3/2015 |

OTHER PUBLICATIONS

Gakhokidze ("Acid Transformation of Hydroxy Aldehydes, Hydroxy Ketones, and Aldoses by the Danilov-Venus-Danilova Reaction," Tbilisi State University, Translated from Zhurnal Obshchei Khimii, 46(7):1620-1628, Published Jul. 1976) (Year: 1976).*
'AWS (American Welding Society, Published 2005) (Year: 2005).*
AWS (American Welding Society) Published 2005.
Gakhokidze, R.A., "Acid Transformation of Hydroxy Aldehydes, Hydroxy Ketones, and Aldoses by the Danilov-Venus-Danilova Reaction," Tbilisi State University, Translated from Zhurnal Obshchei Khimii, 46(7): 1620-1628, Published Jul. 1976. See English translation, pp. 1576-1582.
International Search Report and Written Opinion of related International Application No. PCT/US2016/039282, dated Sep. 8, 2016 (7 pages).
Richards, G.N. "Four-carbon saccharinic acids from the alkaline degradation of 3-0-methyl-L-glycerotetrulose and 4-0-methyl-D-threose", Journal of the Chemical Society 3222-7 Coden: JCS0A9: ISSN: 0368-1769, 1957, XP002787587, DOI: 10.1039/JR9570003222 10.1039/JR9570003222, pp. 3224-3227.
European Office Action from corresponding European application No. 16815388.0, dated Jan. 14, 2019, 6 pages.

* cited by examiner

Primary Examiner — Yevgeny Valenrod
Assistant Examiner — Blaine G Doletski
(74) Attorney, Agent, or Firm — Barnes & Thornburg LLP; Ryan L. Marshall; Jonathan Hartley

(57) ABSTRACT

Methods for the production of 2,4-dihydroxybutyrate (2,4-DHB) from erythrulose and other four-carbon sugars are disclosed. The improved methods facilitate the production of 2,4-DHB that is a precursor for biorenewable and animal nutrition chemicals among others.

20 Claims, No Drawings

METHOD FOR THE PRODUCTION OF 2,4-DIHYDROXYBUTYRIC ACID

This application is a continuation application of U.S. application Ser. No. 15/738,249, filed Dec. 20, 2017, which is a 371 national phase of PCT/US2016/039282, filed Jun. 24, 2016, and claims benefit under 35 U.S.C. § 119(e) of U.S. Provisional Application No. 62/204,796, filed Aug. 13, 2015, and of U.S. Provisional Application No. 62/184,571, filed Jun. 25, 2015, the disclosures of which are incorporated, in their entirety, by this reference. The invention relates to the production of 2,4-dihydroxybutyrate from erythrose and other four-carbon carbohydrates.

TECHNICAL FIELD

Background 2,4-dihydroxybutyrate (also referred to as 2,4-DHB or DHB) is a highly useful chiral intermediate and is of considerable economic interest. DHB can be readily converted into α-hydroxy-γ-butyrolactone in aqueous media by adjusting to the appropriate pH. α-hydroxy-γ-butyrolactone is a prominent precursor for the production of the methionine substitute 2-hydroxy-4-(methylthio)-butyrate (HMTB), as described in U.S. Patent Application 2009/0318715, which has a large market in animal nutrition. DHB is also a promising precursor for biorenewable chemicals such as 3-hydroxypropanal, 3-hydroxypropionic acid, 3-propanediol, and malonic acid. DHB has been produced using complex metabolic engineering approaches as described in U.S. Patent Application Publication No. 2013/0273623, European Patent Application Publication Nos. 2841584 A2 and 2872640 A1. Such metabolic engineering approaches require expensive raw materials and complex reaction conditions. Other synthetic routes have used expensive raw materials such HMTB as described in U.S. Patent Application Publication No. 2013/0204016 A1. There remains a need for cost-effective methods to produce DHB.

The reaction of sugars in alkaline conditions have been studied since the nineteenth century. Sugars react with hydroxide in complicated pathways both in the presence of oxygen and in anaerobic conditions. For example, glucose or fructose react with oxygen gas in an alkaline water solution (see for example, as described in U.S. Pat. Nos. 4,125,559 and 5,831,078), where the 1-2 carbon bond is broken, yielding predominantly formic acid (from carbon 1) and arabinonic acid (from carbons 2-6). Also, large amounts of shorter carbon chain acids also are produced as described in Tapani Vuorinen, "Cleavage of the Intermediate Hydroperoxides in the Oxidation of D-Glucose and D-Fructose with Oxygen," *Carbohydrate Research*, 141 (1985): 319-332. Anaerobic reactions of sugars in alkaline conditions are generally termed degradations and result in complex mixtures of reaction products that are difficult to analyze but that include small amounts of DHB, as described in Byung Yun Yang and Rex Montgomery, "Alkaline Degradation of Glucose: Effect of Initial Concentration of Reactants," *Carbohydrate Research* 280 (1996): 27-45, and J. F. Harris, "Alkaline Decomposition of D-Xylose-1-14C, D-Glucose-1-14C, and D-Glucose-6-14C," *Carbohydrate Research* 23 (July 1972): 207-215. Moreover, compounds such as Class I Caramel Color are created by reacting glucose with hydroxide in anaerobic conditions. Under milder alkaline conditions glucose is known to merely isomerize into fructose, as described in U.S. Pat. No. 3,256,270. Because oxygen is sparingly soluble in water, often degradations occur when open to the atmosphere.

There remains a need in the art for cost effective methods for the production of DHB from four carbon sugars such as erythrose. Erythrose itself is a rare four carbon sugar that has recently been produced on a large scale via electrochemical decarboxylation as described in U.S. Patent Application Publication No. 2007/0181437. The present disclosure provides a method of converting four-carbon sugars, to four-carbon DHB by reacting the sugars in an alkaline solution.

SUMMARY

In one aspect, a method of producing 2,4-dihydroxybutyrate is disclosed which includes mixing a four carbon sugar and a hydroxide salt in solution. In some embodiments, the four carbon sugar may be threose or erythrulose. In some embodiments, the temperature of the solution is maintained below 100° C. In some embodiments, the four carbon sugar is diluted sufficiently to result in a molar yield of DHB that is greater than 40%. The four carbon sugar may be diluted with a solution containing DHB. In some embodiments, the method is carried out in a continuous reactor system. In some embodiments, the hydroxide concentration of the solution may be between about 0.1 M and about 4 M.

In some embodiments, the method includes removing oxygen from the solution. The oxygen may be removed by venting the solution with a gas selected from nitrogen, argon, and mixtures of the same. The oxygen may also be removed by venting the solution with hydrogen.

In some embodiments, the four carbon sugar is erythrose. The erythrose may be diluted with a solution containing one or more other organic acid salts. The erythrose may be diluted with a solution containing DHB.

DETAILED DESCRIPTION

Definitions

"Erythrose" refers to an aldose (tetrose) carbohydrate aldehyde with chemical formula $C_4H_8O_4$, including any stereoisomers, derivatives and analogs thereof. Unless otherwise indicated, recitation of "erythrose" herein is intended to include, without limitation, the molecules: D-(−)-erythrose, L-(+)-erythrose, D-erythrose, L-erythrose, and meso-erythrose. A Fischer Projection of the D-erythrose structure (1) is shown below.

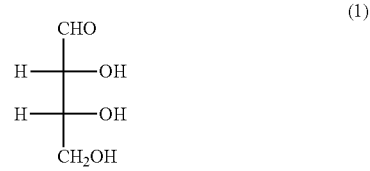

"Threose" refers to an aldose (tetrose) carbohydrate aldehyde with chemical formula $C_4H_8O_4$, including any stereoisomers, derivatives and analogs thereof. Unless otherwise indicated, recitation of "threose" herein is intended to include, without limitation, the molecules: D-(−)-threose, L-(+)-threose, D-threose, L-threose, and meso-threose.

"Erythrulose" refers to a ketose (tetrulose) carbohydrate ketone with chemical formula $C_4H_8O_4$, including any stereoisomers, derivatives and analogs thereof. Unless otherwise indicated, recitation of "erythrulose" herein is intended to include, without limitation, the molecules: D-(−)-erythrulose, L-(+)-erythrulose, D-erythrulose, L-erythrulose.

"2,4-dihydroxybutyrate" (also known as 2,4-DHB or DHB) is an organic acid and refers to the carbohydrate tetronic acid with the chemical formula $C_4H_8O_4$, or salt thereof, including any stereoisomers, derivatives and analogs thereof. Unless otherwise indicated, recitation of "2,4-dihydroxybutyrate" (also known as 2,4-DHB or DHB) herein is intended to include, without limitation, the molecules: (S)-2,4-dihydroxybutyrate, (R)-2,4-dihydroxybutyrate, meso 2,4-dihydroxybutyrate, and 3-deoxytetronate.

As used herein, "derivative" refers to a chemically or biologically modified version of a chemical compound that is structurally similar to a parent compound and (actually or theoretically) derivable from that parent compound. A derivative may, or may not, have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group) that do not substantially alter the function of the molecule for a desired purpose. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, and also salts quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analogue" refers to a chemical compound that is structurally similar to another but differs slightly in composition (as in the replacement of one atom by an atom of a different element or in the presence of a particular functional group), but may or may not be derivable from the parent compound. A "derivative" differs from an "analogue" in that a parent compound may be the starting material to generate a "derivative," whereas the parent compound may not necessarily be used as the starting material to generate an "analogue."

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers. As used herein, the term "about" refers to differences that are insubstantial for the relevant purpose or function.

Alkaline Conversion

The process of converting four carbon sugars to DHB is described below. In some embodiments, a four carbon sugar can be provided as a solution to which hydroxide ion is added in the form of an alkali metal, alkaline earth metal, or ammonium salt, or salt solution. The yield of DHB in these reactions is greatly influenced by the concentration of the sugar and the concentration of hydroxide. At a given temperature, reduced four carbon sugar concentration results in increased DHB yields, and increased hydroxide concentration results in increased DHB yields. At the same hydroxide concentration, increasing the temperature results in increased DHB yields. In some embodiments, erythrose can be provided as the four carbon sugar. In other embodiments, threose or erythrulose can be provided as the four carbon sugar. In one embodiment, the solution is purged with a gas such as nitrogen, hydrogen, or argon or mixtures of the same to remove oxygen from the solution.

In some embodiments, the alkaline conversion of a four carbon sugar into DHB by introducing a solution of the four carbon sugar into a continuous reactor holding sufficient solution to dilute the four carbon sugar to result in high yields of DHB. In such a reactor, the four carbon sugar would be diluted by a solution contain hydroxide salt, DHB, and/or other organic acid salts. The reactor includes the means to maintain the solution at specific temperature, and the means to introduce the solution of the four carbon sugar, a solution of hydroxide salt, and the means to remove product.

EXAMPLES

Example 1

A 153 gram erythrose per liter solution in water was provided. Table 1 provides the results of experiments where the indicated volume of the erythrose solution was add to 10 ml of 1 M sodium hydroxide in water. The mixtures were stirred for 60 min at the indicated temperature.

TABLE 1

| Sample ID | Erythrose Solution Vol. (mL) | Temp (C.) | Yield (DHB) on erythrose % |
|---|---|---|---|
| 921-91-3 | 1 | 22 | 16% |
| 921-91-4 | 2 | 22 | 12% |
| 921-91-5 | 5 | 22 | 2% |
| 921-93-1 | 1 | 40 | 57% |
| 921-93-2 | 2 | 40 | 34% |
| 921-93-3 | 5 | 40 | 13% |
| 921-95-1 | 1 | 50 | 64% |
| 921-95-2 | 2 | 50 | 44% |
| 921-95-3 | 5 | 50 | 18% |
| 921-95-4 | 1 | 60 | 56% |
| 921-95-5 | 2 | 60 | 41% |
| 921-95-6 | 5 | 60 | 20% |

Example 2

A 156 gram erythrose per liter solution in water was provided. 1 mL of the erythrose solution was added to 100 mL of the indicated hydroxide solution in Table 2 and stirred at 40° C. for 60 minutes.

TABLE 2

| Exp. | Caustic | 2,4-DHB Yield |
|---|---|---|
| 953-31-4 | 4M KOH | 59% |
| 953-33-1 | 4M NaOH | 58% |
| 953-33-3 | 3.5M LiOH | 53% |

Example 3

A 153 gram erythrose per liter solution in water was provided. 1 mL of the erythrose solution was add to 100 mL of a 4 M sodium hydroxide solution that also had a concentration of the organic acid salt sodium arabonate of 2.4 M. The solution mixed for 60 minutes at 40 C. DHB was quantified showing a molecular yield of greater than 58%.

Example 4

A 100 ml reactor was provided containing 4 M NaOH and heated to 50° C. A 80 gram erythrose per liter solution in water was provided. 1 mL of the erythrose solution was added to the reactor per minute, and 45% NaOH was added at a rate of 0.19 mL per minute. 1 ml of the erythrose solution was added to a 4 M sodium hydroxide solution and stirred under argon. The solution was maintained at 30° C. for 60 min. The reactor volume was maintained constant throughout the experiment. After 4 hours the solution in the reactor was analyzed by HPLC and DHB was quantified showing a molecular yield of 46%.

Example 5

1 L high pressure reactor with headspace entraining hollow-shaft mixer was provided. 700 mL of a 4 M NaOH solution was provided and the reactor was heated to 50° C. The reactor was then pressurized with the gases outlined in Table 3 to 750 psi. 7 mL of a 136 g per L erythrose solution was then added to the reactor. After 60 minutes, the solutions were then analyzed by HPLC.

TABLE 3

| Gas | DHB % Yield |
|---|---|
| Air | 34% |
| Oxygen | 0% |
| Hydrogen | 50% |

Example 6

100 mg of threose was added to 50 mL of a 4 M sodium hydroxide solution and stirred at 40° C. for 60 min. DHB was quantified showing a molecular yield of greater than 56%.

Example 7

A 152 gram erythrulose per liter solution in water was provided. 1 mL of the erythrulose solution was added 100 mL of 2M NaOH solution. The solution was then stirred at 50° C. for 15 min. DHB was quantified showing a molecular yield of 65%.

Example 8

A 136 gram erythrose per liter solution in water was provided. 1 mL of the erythrose solution was added 200 mL of 4 M NaOH solution under a hydrogen headspace. The solution was then stirred at 40° C. for the times indicated in Table 4.

DHB yields are also reported in Table 4.

TABLE 4

| Sample | Min | DHB % yield |
|---|---|---|
| 953-66-2 | 2 | 12% |
| 953-66-3 | 5 | 30% |
| 953-66-4 | 10 | 47% |
| 953-66-6 | 35 | 58% |
| 953-66-7 | 60 | 60% |
| 953-66-8 | 104 | 64% |

Example 9

A 132 gram erythrose per liter solution in water was provided. 1 mL of the erythrose solution was added 100 mL of 1 M BaOH. The solution was then stirred at 60° C. for 100 min. DHB was quantified showing a molecular yield of 20%.

Example 10

A 135 gram erythrose per liter solution in water was provided. 1 mL of the erythrose solution was added 100 mL of NaOH solution with a concentration indicated in Table 5. The solution was then stirred at 50° C. for 35 min. DHB was quantified showing a molecular yield indicated in Table 5.

TABLE 5

| Sample | M NaOH | Yield DHB |
|---|---|---|
| 953-70-4 | 1 | 41% |
| 953-70-13 | 2 | 54% |

Example 11

A 135 gram erythrose per liter solution in water was provided. 1 mL of the erythrose solution was added to 100 mL of saturated Lead Hydroxide solution. The solution was then stirred at 50° C. for 60 min. DHB was quantified and no DHB was present in the reaction solution.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

STATEMENTS

1. A method of producing 2,4-dihydroxybutyrate, comprising: mixing a four carbon sugar and an hydroxide salt in solution.
2. The method of 1, wherein the four carbon sugar is erythrose.

3. The method of 1, wherein the four carbon sugar is threose or erythrulose.

4. The method of any one of 1-3, wherein the hydroxide concentration of the solution is between 0.1 M and 4 M.

5. The method of any one of 1-4, wherein the temperature of the solution is maintained below 100° C.

6. The method of any one of 1-5, wherein the four carbon sugar is diluted sufficiently to result in a molar yield of DHB that is greater than 40%.

7. The method of any one of 1-6, wherein the four carbon sugar is diluted with a solution containing DHB.

8. The method of any one of 1-7, wherein the erythrose is diluted with a solution containing one or more other organic acid salts.

9. The method of any one of 7-8, wherein the method is performed in a continuous reactor system.

10. The method of any one of 1-9, further comprising removing oxygen from the solution.

11. The method of 10, wherein oxygen is removed by venting the solution with a gas selected from the group consisting of: nitrogen, argon, and mixtures of the same.

12. The method of 10, wherein oxygen is removed by venting the solution with hydrogen.

We claim:

1. A method of producing 2,4-dihydroxybutyrate (DHB), comprising: mixing a four carbon sugar and a hydroxide salt in solution, wherein the four carbon sugar is erythrulose.

2. The method of claim 1, wherein the temperature of the solution is maintained below 100° C.

3. The method of claim 1, wherein the four carbon sugar is diluted sufficiently to result in a molar yield of DHB that is greater than 40%.

4. The method of claim 1, wherein the four carbon sugar is diluted with a solution containing DHB.

5. The method of claim 1, wherein the method is performed in a continuous reactor system.

6. The method of claim 1, wherein the hydroxide concentration of the solution is between 0.1 M and 4 M.

7. The method of claim 6, wherein the temperature of the solution is maintained below 100° C.

8. The method of claim 7, wherein the four carbon sugar is diluted with a solution containing DHB.

9. The method of claim 1, further comprising removing oxygen from the solution.

10. The method of claim 9, wherein oxygen is removed by venting the solution with a gas selected from the group consisting of: nitrogen, argon, and mixtures thereof.

11. The method of claim 9, wherein oxygen is removed by venting the solution with hydrogen.

12. The method of claim 11, wherein the temperature of the solution is maintained below 100° C.

13. The method of claim 12, wherein the erythrulose is diluted with a solution containing one or more other organic acid salts.

14. The method of claim 13, wherein the method is performed in a continuous reactor system.

15. A method of producing 2,4-dihydroxybutyrate, comprising:
mixing a four carbon sugar and a hydroxide salt in solution; and
removing oxygen from the solution by venting the solution with hydrogen,
wherein the four carbon sugar is erythrulose.

16. The method of claim 1, wherein the four carbon sugar is D-(−)-erythrulose, L(+)-erythrulose, D-erythrulose, L-erythrulose, or any combination thereof.

17. The method of claim 1, wherein the four carbon sugar is D-(−)-erythrulose, L(+)-erythrulose, D-erythrulose, L-erythrulose, a salt thereof, a hydrate thereof, or any combination thereof.

18. The method of claim 15, wherein the four carbon sugar is D-(−)-erythrulose, L(+)-erythrulose, D-erythrulose, L-erythrulose, or any combination thereof.

19. The method of claim 15, wherein the four carbon sugar is D-(−)-erythrulose, L(+)-erythrulose, D-erythrulose, L-erythrulose, a salt thereof, a hydrate thereof, or any combination thereof.

20. The method of claim 15, wherein the temperature of the solution is maintained below 100° C.

\* \* \* \* \*